(12) United States Patent
Cohen-Bacrie et al.

(10) Patent No.: US 6,176,827 B1
(45) Date of Patent: Jan. 23, 2001

(54) METHOD OF DETECTING ELASTICITY VARIATIONS AND ECHOGRAPHIC APPARATUS FOR CARRYING OUT THE METHOD

(75) Inventors: Claude Cohen-Bacrie, Paris; Claire Le Floch, Nogent-sur-Marne, both of (FR)

(73) Assignee: U.S. Philips Corporation, New York, NY (US)

(*) Notice: Under 35 U.S.C. 154(b), the term of this patent shall be extended for 0 days.

(21) Appl. No.: 09/313,039

(22) Filed: May 17, 1999

(30) Foreign Application Priority Data

May 19, 1998 (FR) .................................................. 9806311

(51) Int. Cl.$^7$ ...................................................... A61B 8/00
(52) U.S. Cl. ............................................................ 600/438
(58) Field of Search .................................. 600/438, 447, 600/443, 437, 448

(56) References Cited

U.S. PATENT DOCUMENTS 5,579,771 * 12/1996 Bonnefous ............................ 600/443
5,806,520 * 9/1998 Berger et al. ........................ 600/443

OTHER PUBLICATIONS

"Tissue Elasticity Reconstruction Using Linear Perturbation Method" by F. Kallel and M. Bertrand, IEEE Transactions on Medical Imaging, vol. 15, No. 3, Jun. 1996, pp. 299–313.

\* cited by examiner

*Primary Examiner*—Marvin M. Lateef
*Assistant Examiner*—Maulin Patel
(74) *Attorney, Agent, or Firm*—Dwight H. Renfrew

(57) ABSTRACT

A method of detecting elasticity variations in a soft tissue which is subjected to an external compression in a predetermined axial direction includes the steps of:

estimating a field of axial displacements in the tissue, determining an elasticity modulus estimator, including an operation for minimizing a distance between an image of a distribution of elementary elasticity moduli, by a Finite Element Model, and the axial displacement field, and regularizing the solution of the estimator by means of a diagonal matrix (R) whose coefficients $\alpha_{ii}$ are functions of the axial displacements ($d_i$) and are applied to the respective values of the elementary elasticity moduli ($e_i$) in order to ensure that these elementary elasticity modulus values remain within an uniform interval which is centered around a mean value of each elementary modulus.

12 Claims, 4 Drawing Sheets

METHOD OF DETECTING ELASTICITY VARIATIONS AND ECHOGRAPHIC APPARATUS FOR CARRYING OUT THE METHOD

FIELD OF THE INVENTION

The invention relates to a method of detecting elasticity variations in a soft tissue which is subjected to an external compression in a predetermined axial direction.

The invention also relates to an echographic apparatus provided with means for carrying out the method.

The invention is used in the medical imaging industry.

BACKGROUND OF THE INVENTION

A method of reconstructing tissue elasticity while using linear perturbation is already known from the publication "Tissue Elasticity Reconstruction Using Linear Perturbation Method" by F. Kallel and M. Bertrand, IEEE TRANSACTIONS ON MEDICAL IMAGING, VOL. 15, No. 3, JUNE 1996, pp. 299–313. Said publication describes a method of reconstructing the elasticity modulus of a soft tissue, which is subjected to a static external compression, on the basis of measurements of displacements caused by said compression. Said method utilizes a known algorithm for solving an inverse problem; this algorithm is called the Newton-Raphson algorithm and utilizes a direct relation which yields the image of a set of displacement fields by way of a Finite Element Model of elasticity equations and adapts said direct relation, in a least squares sense, in order to provide the distribution of the corresponding elasticity moduli. The set of axial displacement fields of tissues forms the basic data which is estimated in advance while utilizing a multi-bit correlation technique which is applied to ultrasonic signals. The problems relating to the matrix enabling the solution of the inverse problem according to the Newton-Raphson algorithm are taken into account while utilizing a known so-called Tikhonov regularization technique which utilizes the identity matrix I. A regularization technique is used so as to realize a compromise between the reliability of the data observed and the a priori information of the solution. Utilizing an echographic imaging model, said publication teaches that the algorithm converges in from 10 to 15 iterations. Figures of the cited publication show images of the elasticity modulus distribution obtained in 15 iterations by reconstruction on the basis of noisy data while utilizing the Newton-Raphson algorithm regularized for each iteration by the Tikhonov term with I.

SUMMARY OF THE INVENTION

In the field of medical diagnosis of anomalies in soft tissues, malignant tumors are distinct from healthy tissue and from benign tumors that the elasticity of these tissues differs; this difference is due to their different structure. In the field of breast cancer diagnosis it is particularly interesting to have a non-invasive measuring method available which is exact as well as reliable for the detection of malignant tumors, that is to say skin deep tumors as well as very deep tumors and starting tumors of very small diameter which are very difficult to detect.

It is a problem that the distribution of the elasticity modulus in a soft tissue cannot be measured directly. Only the field of displacements due to a compression of the soft tissue can be measured. However, such displacements are extremely small, so that the measurements thereof cannot be used directly by a practitioner. Conversely, the elasticity modulus distribution forms a set of data which is very interesting because of the fact that this data offers suitable information as regards the nature of the tissues and has a significant contrast which can be readily used and is linked to the measurements of displacements caused by a compression of the soft tissue. Another problem is that the elasticity modulus distribution is not linked to the data of the displacement field by way of a direct relation. On the other hand, the data of the displacement field is linked to the elasticity modulus distribution by way of a direct relation, with the result that the elasticity modulus distribution in a tissue must be calculated by means of a method for solving the inverse problem on the basis of data of the displacement field. A method of solving an inverse problem is already described in the cited publication. It is a problem that this known method is not exact enough for use for the detection of malignant tumors by determination of the elasticity modulus distribution in tissue, because the measured data of the displacement field is very small and the presence of the noise during the acquisition of this data is extremely pronounced.

Therefore, the invention proposes a detection method as disclosed in claim 1.

This method offers reconstruction images of elasticity variations in the tissue which are far less noisy, have more contrast and hence enable the detection of very small elasticity variations which correspond to inhomogeneities of the tissue, and hence enable better localization of these defects. This offers improved possibilities for applying this method for the detection of very small tumors.

The method is advantageously carried out by means of an echographic apparatus which constitutes a non-invasive diagnostic tool.

BRIEF DESCRIPTION OF THE DRAWINGS

The invention will be described in detail hereinafter with reference to the accompanying diagrammatic drawings; therein.

DESCRIPTION OF PREFERRED EMBODIMENTS

The invention relates to a method for the processing of an echographic signal in order to detect inhomogeneities in an explored medium, that is to say a medium subjected to ultrasound signals emitted and received by an echography apparatus. The invention is based on the processing of the echographic signal in order to determine the distribution of the elasticity modulus in the explored medium while using a regularized inverse solving method, applied to data of a field of displacements measured in said medium. The invention can be very attractively applied for the detection of malignant tumors by determination of the distribution of the elasticity modulus in the tissues, as well as for the determination of the size of such tumors.

Figure 1:
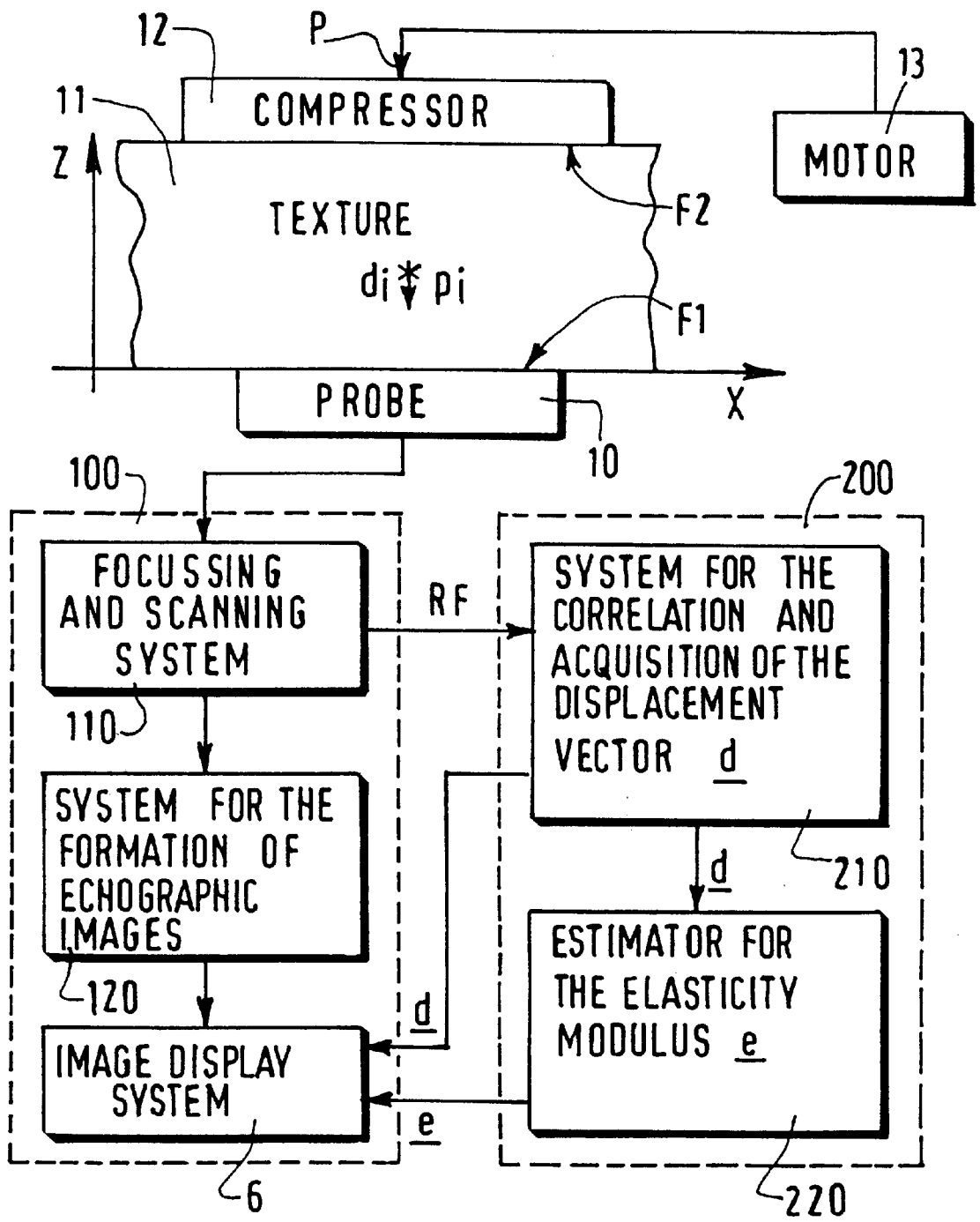
FIG. 1 shows a block diagram of the systems carrying out the steps of the method for detecting inhomogeneities in tissue.

The medium in FIG. 1 is, by way of example, breast tissue which is called texture 11. A continuously variable pressure P is applied to the breast tissue and a displacement field is determined by subjecting a region of the tissue to ultrasound signal excitations and by applying a correlation method to the ultrasound signals. More specifically, the pressure P continuously increases and is applied by means of a compressor 12 which is driven by a motor 13. The zone 11 of the breast tissue which is subjected to the compression has a fixed face F1 whereto a probe 10 of an echography apparatus 100 is applied, and a parallel face F2 whereto the pressure P of the compressor is applied in the perpendicular direction. In the device according to the invention as shown in FIG. 1, the mobile wall of the compressor 12 applied to the face F2 is displaced in the direction of the face F1 at a given speed $\vec{v}$. The probe 10 applied to the fixed face F1 applies RF signals to the texture 11 during excitations parallel to the direction of the face F2. The excitation lines along the axis Z extend perpendicularly to the faces F1 and F2 and parallel to the direction of the pressure of the compressor 12. The excitations are produced by the echography apparatus 100 which includes a system 110 for focusing the RF signals in the tissue 11, parallel to an axis Z, and for scanning by way of the excitation signals RF linearly parallel to an axis X which extends parallel to the face F1. The scanning according to the axis X is performed along a given number of N excitation lines with a recurrent period T. When the N excitations from 1 to N parallel to Z have been performed, the probe starts anew with N excitations from 1 to N with a period NT for a given excitation line. The probe in return receives from the texture 11 the echographic signals which are applied to an elasticity variation detection system 200. Preferably, the probe consists of an array of linear detectors emitting recurrent excitations. The system 200 includes a 1-bit temporal correlation system 210 for performing in real time the correlation of each of the signals transmitted by the probe and originating from a given location in the texture 11. The correlation system 210 executes the correlation of signals relating to two successive excitations of the probe and originating from a given location, and provides the amplitude of the displacements of each point of the structure 11 explored by the probe on each excitation line. During the operation of the compressor 12, this method supplies, continuously and in real time, an image of the displacement field of the structures forming the texture 11.

Figure 3:
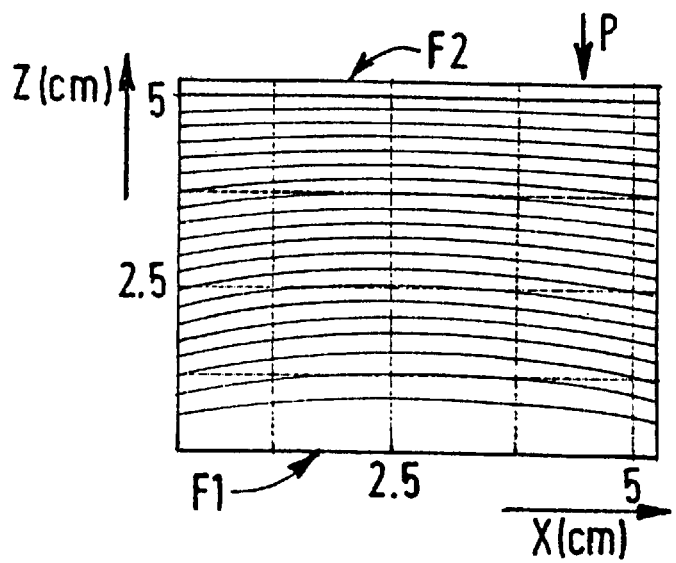
FIG. 3 shows iso-displacement lines of a displacement field, calculated on the basis of echographic signals acquired during the compression of an explored tissue.

To this end, the image of the displacement field in the zone of the explored texture 11 is discretized. The signals produced by the various scans by the probe are not stored. These signals are correlated directly by the 1-bit temporal correlation system 210 which provides an image of the displacements of each point of the structure, for example in the form of iso-displacement lines as illustrated in FIG. 3. The present method also involves specific means for making the determination of the distribution of the elasticity modulus distribution resistant to noise in order to realize, in combination with a reconstruction of the elasticity modulus distribution which is realized in real time, a reconstruction which is less noisy than that achieved according to the state of the art.

It is to be noted that the displacements calculated by the correlation system 210 result from direct measurements of the displacements of the structures of the region explored by means of the echography apparatus. These displacements are radial, parallel to the pressure P and are obtained under the influence of said external pressure P exerted on the tissue 11.

Preferably, several series of scans are performed while using therebetween an equal compression or a displacement, equal to $\vec{v} \times NT$, of the face F2 of the compressor, followed by averaging of the data supplied by the correlation system 210. This method enables a high precision to be achieved in this step 210 for the acquisition of the displacement field.

In the step 210 the data of the displacement field is calculated in the form of elementary displacements $d_l, \ldots d_i \ldots d_n$ for each pixel of the discretized ultrasonic image obtained by way of the correlation method. The data of the elementary displacements constitutes a displacement data vector $\underline{d}$.

This displacement vector $\underline{d}$ is linked to a so-called elasticity modulus vector (or Young modulus) $\underline{e}$ by a direct relation F which is written as (1):

$$\underline{d} = F(\underline{e}) \tag{1}$$

The elasticity modulus vector $\underline{e}$ is formed by elementary elasticity moduli $e_l, \ldots e_i \ldots e_n$ which correspond to the respective elementary displacements relating to each pixel $p_l, \ldots p_i, p_n$ of the discretized image. It is known that $F(\underline{e})$ is the image realized by means of a Finite Element Model of the distribution of the elementary elasticity moduli, that is to say of the vector $\underline{e}$. A Finite Element Model is a calculation technique which can be applied to the elasticity equations and is known to those skilled in the art.

The problem to be effectively solved is the determination of the vector $\underline{e}$ giving the distribution of the elasticity modulus in the explored region having produced the displacement field. The determination of the vector $\underline{e}$ enables the formation of an image of the elasticity modulus distribution which is formed by elementary moduli relating to each pixel of the discretized image.

The value of the vector $\underline{e}$ is obtained, on the basis of the relation (1), by solving the inverse problem according to the relation (2):

$$\hat{e} = \arg\min[\|d - F(\underline{e})\|^2] \tag{2a}$$

where $\hat{e}$ is an estimator of $\underline{e}$. The estimator $\hat{e}$ of the elasticity modulus $\underline{e}$ minimizes the distance $\|d - F(\underline{e})\|^2$ between the data d acquired by means of the measurements in the step 210 of FIG. 1 and the image $F(\underline{e})$ realized by means of the Finite Element Model. The estimator $\hat{e}$ enables determination of the vector $\underline{e}$ which, once it has been inserted into the Finite Element Model, yields a value of the vector $\underline{d}$ which approximates as closely as possible the vector $\underline{d}$ measured in the step 210.

The relation (2a) is known from the publication cited as the state of the art and is called the Newton-Raphson algorithm. This algorithm enables calculation of the minimum value of the distance $\|d - F(e)\|^2$ in an iterative manner, for example by means of 10 or 15 iterations according to the state of the art. The Newton-Raphson algorithm utilizes an iterative minimization of the distance which is written as:

$$[d-F(\underline{e})]^T[d-F(\underline{e})] \quad (2b)$$

This minimization is performed by means of successive first-order linear approximations of F. The first iteration of this algorithm enables the problem of linear estimation of the vector $\underline{e}$ to be dealt with by solving the inverse problem associated with the direct problem whose equation is:

$$\underline{d} = S\underline{e} + b \quad (3)$$

where S is a so-called sensitivity matrix for which a calculation method is described in the publication cited as the state of the art and which is a function of $\underline{d}$, and where b is a Gaussian white noise. As a result, the first iteration of the Newton-Raphson algorithm is written in a novel way in conformity with the following relation (4):

$$\hat{e} = \arg\min[\underline{d} - S\underline{e}]^T[\underline{d} - S\underline{e}] \quad (4)$$

This known algorithm has recognized drawbacks which are essentially problems concerning convergence of the algorithm and problems concerning instability of the solution, which problems are linked to the noise which is generally pronounced in the image of the displacement distribution obtained by ultrasound. An inverse problem, whose solution is unstable because of the noise, is not a well-posed problem. According to the publication cited as the state of the art, this problem is solved by the Tikhonov regularization method which consists in applying a regularization term to the Newton-Raphson algorithm (4) according to the relation (5):

$$^T(\underline{d} - S\underline{e}) + \lambda \underline{e}^T I \underline{e}] \quad (5a)$$

The Tikhonov regularization term is written as:

$$\lambda \underline{e} I^T \underline{e}$$

and is a "smoothing" constriction applied to the Newton-Raphson algorithm in order to reduce the effect of the noise. This term smoothes the solution of the estimator by applying completely equal regularization coefficients to all elementary elasticity moduli $e_1, \ldots e_i, \ldots e_n$. In other words, in the regularization term the regularization matrix is the identity matrix I whereto completely equal coefficients are assigned. This means that in the equation (3), in which the estimator ê calculates a minimum, the distance and the regularization term must both be as small as possible. The Tikhonov regularization term can be written in a manner known to those skilled in the art as:

$$\lambda \underline{e} I^T \underline{e} = \lambda [e_1^2 + e_2^2 + \ldots e_i^2 + \ldots + e_n^2] = \lambda \sum_{i=1}^{i=n} e_i^2 \quad (7a)$$

where the values $e_i$ are the elementary moduli $e_1$ to $e_n$ of the vector $\underline{e}$. The Newton-Raphson algorithm, whereto the Tikhonov regularization is applied during each iteration, selects the solution where all $e_i$ are pushed towards zero by the same force. According to this regularization method it is assumed that the information contained in the displacement field relating to the elasticity modulus of an element $e_i$ of $\underline{e}$ is independent of the location of $e_i$ which is concretized by the index i. However, unfortunately, this ideal situation is never reached.

Therefore, the invention proposes a novel regularization method which is very resistant to noise and intended to be applied to the Newton-Raphson algorithm. Among the problems intended to be solved by the present invention there is the fact that the measurement of the displacement field linked to the elasticity modulus vector by the direct relation (1) suffers from noise and the fact that this measurement is dependent on the zone of the explored region in which it has been acquired; therefore, the data originating from different explored zones cannot be treated in an undifferentiated manner. The regularization method according to the invention, therefore, is based on the recognition of the fact that the explored region includes zones which contain information of a level which is much higher than in other zones. Consequently, the regularization method according to the invention is based on a determination of coefficients or weights to be assigned to each element of the elasticity modulus vector in other to take into account the variability of measurements of the displacement and of the reliability attached to this information due to their level, resulting from these measurements, and due to their location within the explored region.

In the formule (5a) according to the state of the art, the Newton-Raphson algorithm regularized by the Tikhonov term performs, during each iteration, the minimization of a cost function C which is written as:

$$C = [(\underline{d} - S\underline{e})^T(\underline{d} - S\underline{e}) + \lambda \underline{e}^T I \underline{e}] \quad (6)$$

enabling the Newton-Raphson algorithm regularized by the Tikhonov term to be expressed in a new form as:

$$\hat{e}_i = \arg\min[S^T S + \lambda I]^{-1} S^T d \quad (5b)$$

The Tikhonov regularization term, which was $$\lambda I \quad (8a)$$

in the formule $\hat{e}_i$ (5b) of the known Newton-Raphson algorithm, is transformed according to the invention into a new regularization matrix which is expressed as:

$$R \quad (8b).$$

According to the invention, the regularization term is formed while using a matrix R which is different from the identity matrix I multiplied by the Tikhonov constant $\lambda$ and by explicitly calculating the coefficients $\alpha_i$ of this new regularization matrix (R). The foregoing deviates from the Tikhonov regularization where the coefficients of the regularization matrix I, as given by the relation (6), are all equal. Thus, according to the invention all coefficients $\alpha_i$ of the regularization matrix R are potentially different in order to be adapted to the data $d_i$ of the displacement field measured for each pixel of the explored region, so that each point $e_i$ of the reconstruction image of the elasticity modulus distribution is formed by an element $\alpha_i e_i$ of the elasticity modulus vector which is specifically adapted to a corresponding data $d_i$ of the displacement field.

This results in a regularized Newton-Raphson algorithm according to the invention which is written in conformity with the following formule (9a):

$$\hat{e}_R = \arg \text{Min}[(\underline{d} - S\underline{e})^T(\underline{d} - S\underline{e}) + \underline{e}^T R \underline{e}] \quad (9a)$$

which can be written as (9b):

$$\hat{e}_R = \arg\min[S^T S + R]^{-1} S^T d \quad (9b)$$

According to the invention the regularization term R can thus be written in conformity with the relation (7b) while utilizing the writing means of the relation (7a), thus yielding:

$$e^T R \underline{e} = \alpha_1 e_1^2 + \alpha_2 e_2^2 + \ldots \alpha_i e_i^2 \ldots + \alpha_n e_n^2 = \sum_{i=1}^{i=n} \alpha_i e_i^2 \quad (7b)$$

This relation (7b) expresses that the diagonal elements of the matrix R constitute the coefficients $\alpha_i$ which are applied to all of the respective elements $e_i$ of the elasticity modulus vector $\underline{e}$.

Figure 2:
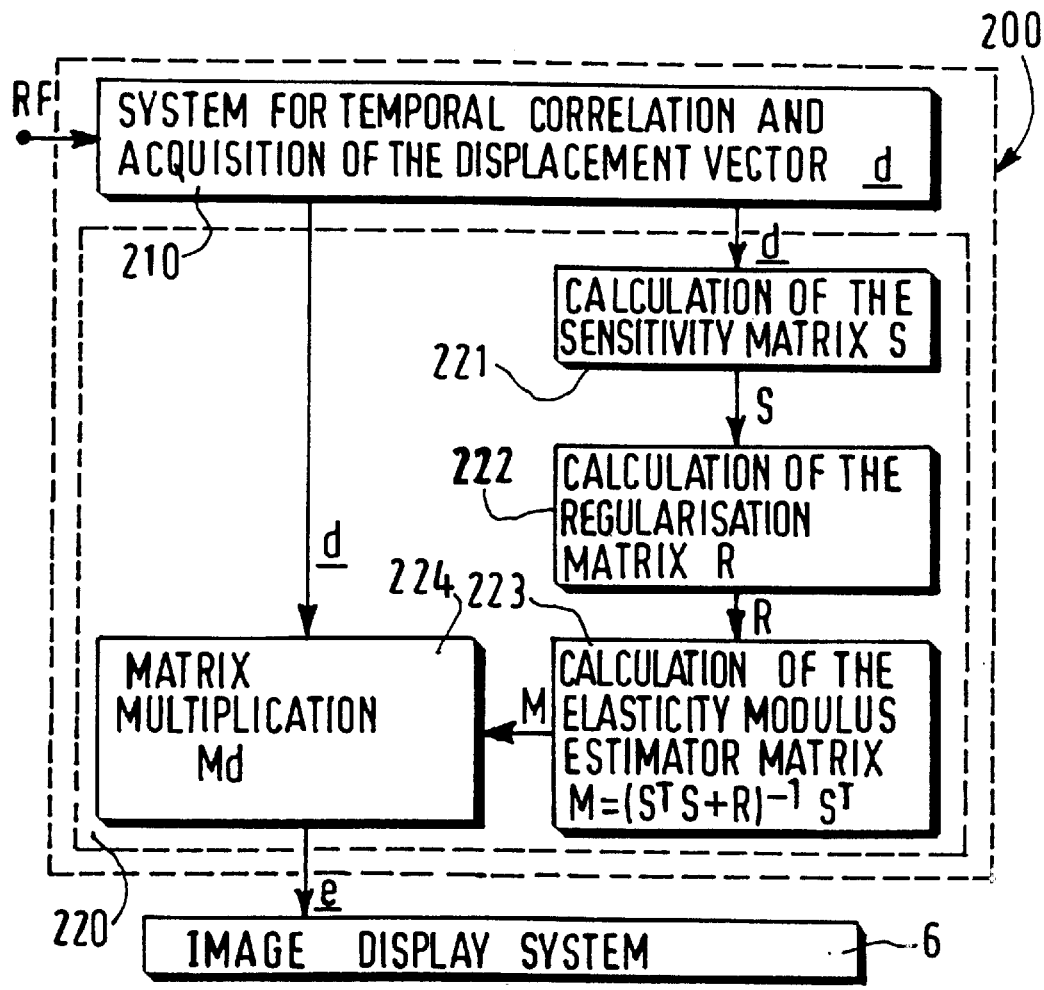
FIG. 2 shows a block diagram of the systems carrying out the functional steps for reconstructing the elasticity modulus distribution on the basis of the displacement field.

Referring to FIG. 2, the invention proposes an electronic system 200 which is associated with the echography apparatus and can operate in real time in order to carry out an attractive method of determining said coefficients $\alpha_i$ so as to form coefficients or weights to be applied to the elements $e_i$. The system 200 executes:

- a step 210 for the acquisition of the displacement field or displacement vector $\underline{d}$ by 1-bit temporal correlation of the RF signals transmitted by the probe;
- a step 220 for estimating the elasticity modulus vector $\underline{e}$ which includes:
- an operation 221 for calculating the sensitivity matrix S as is known, for example from the cited publication;
- an operation 222 for calculating the regularization matrix R, including:
- a sub-operation for truncated decomposition of the sensitivity matrix S into single values. It will be recalled that the operation for the decomposition of a matrix into single values consists in writing the relevant matrix on a base of real vectors as is known to those skilled in the art. Such a decomposition defines new matrices with a change of reference matrix V and a diagonal matrix $\Delta$ formed by elements $\delta_{ii}$. According to the invention, the truncation level for performing the truncated decomposition has been empirically determined and has been found to be preferably of the order of from 0.2 to 10%. The diagonal matrix $\Delta$ is used to construct a new diagonal matrix K whose diagonal elements are calculated in conformity with the following formule (11a):

$$K_{ii} = (\Delta_{ii}/cte)) - \Delta_{ii}^2 \quad (11a)$$

- a sub-operation for the actual calculation of the regularization matrix R according to the invention, being a diagonal matrix whose diagonal elements $\alpha_{ii}$, also called $\alpha_i$, are the diagonal elements of a matrix J which is not necessarily diagonal and is obtained by way of the following formula (11b):

$$J = VKV^T \quad (11b)$$

According to the invention, the regularization term smoothes the distribution of the elements of the elasticity modulus by means of a vector which is formed by diagonal coefficients of the matrix R, thus forcing given pixels of the image to have elements $e_i$ which tend more strongly to zero than others. The regularization function according to the invention defines a uniform interval and forces each value $e_i$ to remain within this interval which is centered around a specific mean value $e_{Mi}$ of $e_{ei}$. Thus, the definition of the regularization matrix R according to the invention enables the vector, formed by distances from the mean value of $e_i$, to remain uniform. This regularization method enables a reconstructed image of the modulus distribution e of the object to be obtained by means of an estimator ê of $\underline{e}$ whose sensitivity to noise is uniformly distributed between all the components $e_i$ from $e_l$ to $e_n$ of $\underline{e}$. The diagonal coefficients of the regularization matrix R weight the respective elementary components $e_i$ in a manner which is potentially different as a function of their location i. This method of regularization is very resistant to the noise. According to the invention, the uniform interval is defined and the regularization matrix R is derived from the sensitivity matrix S by simple matrix calculations (described above) which are performed in the system 200 as shown in FIG. 1.

At the end of the operation 222 for calculating the matrix R, the electronic system 200 associated with the echography apparatus executes:

- an operation 223 for calculating the matrix M of the estimator of $\underline{e}$ on the basis of the relation (9b) in conformity with the relation:

$$M = [S^T S + R]^{-1} S^T \quad (10),$$

followed by an operation 224 for matrix multiplication of the matrix M by the vector $\underline{d}$.

According to the invention a single iteration suffices so as to obtain a reconstruction image of the elasticity modulus $\underline{e}$ on the basis of the displacement vector $\underline{d}$ while utilizing the method which is represented by the functional blocks in FIG. 1 and carried out by the electronic system 200 associated with the echography apparatus 10, 100 of FIG. 1. The regularization term is thus applied to this single iteration. This results in the simple implementation of the invention as illustrated by FIG. 2 in association with FIG. 1.

The FIGS. 4, 5A, 5B and 6A, 6B illustrate the results obtained by means of the method according to the invention. These Figures can be displayed by means of a display system 6 which includes a monitor, and possibly recording means, associated with the echography apparatus 100. This display system is, for example the same system as that enabling the display and recording of echographic images via the imaging system 120.

Figure 4:
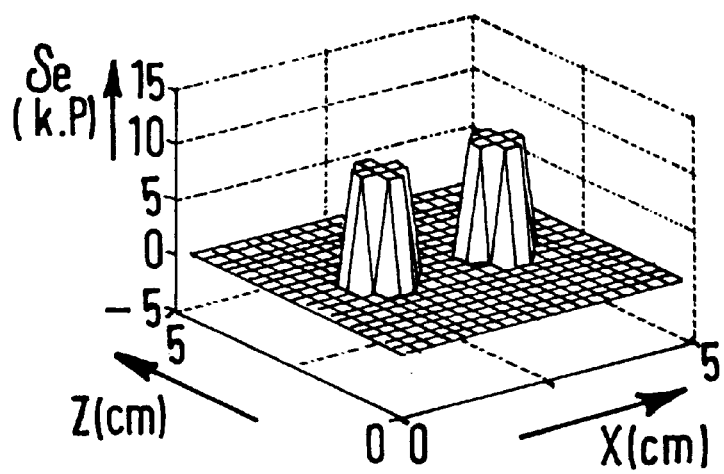
FIG. 4 shows an image of the variations of the elasticity modulus in a tissue with two inhomogeneities.

FIG. 4 shows a discretized explored tissue zone having a width of 5 cm in the direction X and a thickness of 5 cm in the direction Z. The tissue contains two inclusions or inhomogeneities, resulting in variations of the elasticity modulus which are expressed as $\Sigma e$ in kilopascals and appear in the form of two regular reliefs.

Figure 5A:
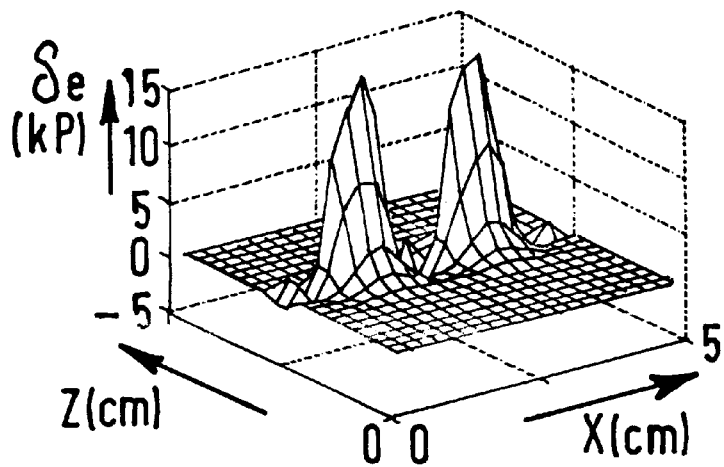
FIGS. 5A, 5B show an image of the variations of the elasticity modulus obtained by the linear Newton-Raphson method regularized by means of a regularization method according to the invention in the case of signal-to-noise ratios equal to 50 and 20, respectively, with a single iteration and in conformity with FIG. 4.
Figure 5B:
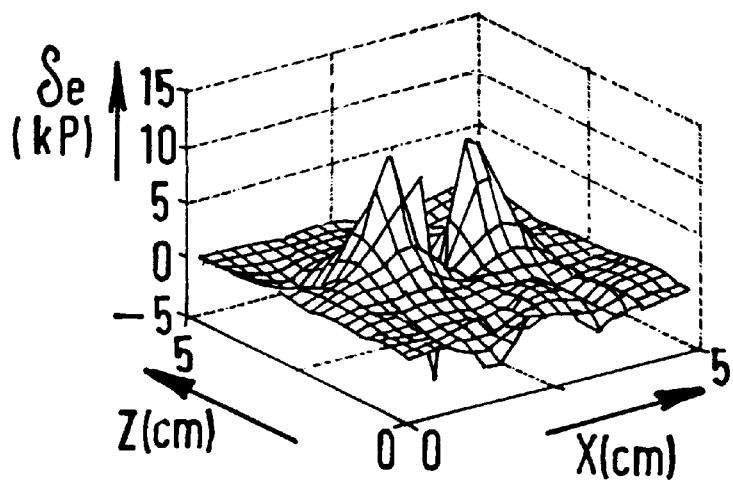

FIGS. 5A and 5B are reconstructions utilizing the regularization matrix R according to the invention on the basis of displacement data determined by means of the echographic method illustrated by the FIGS. 1 and 2 for the variations $\delta e$ of the elasticity modulus, using the same units, in the case where, moreover, the displacement data contains noise. FIG. 5A has been formed for a signal-to-noise ratio equal to 50 and FIG. 5B for a signal-to-noise ratio equal to 20.

Figure 6A:
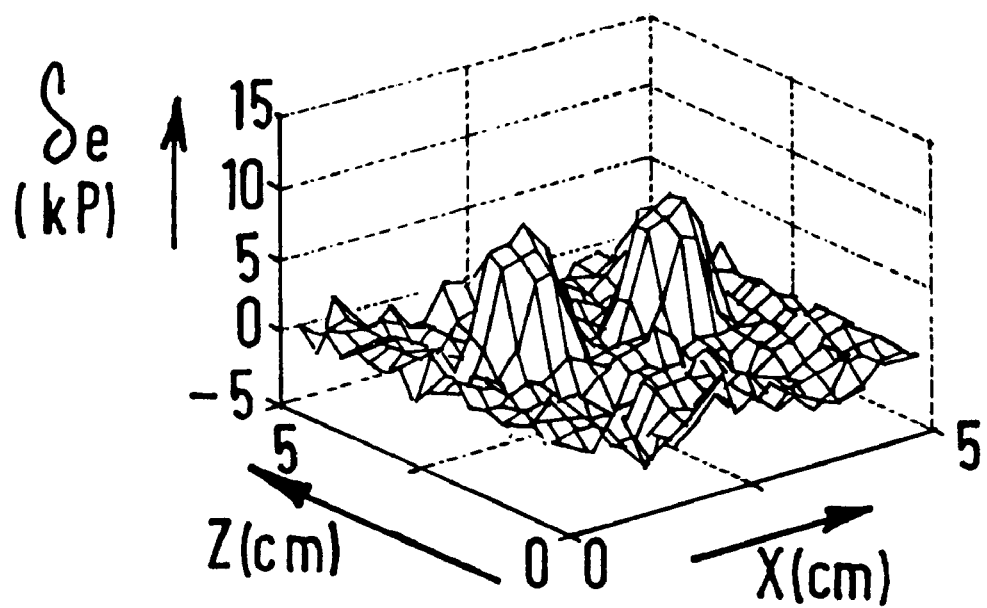
FIGS. 6A, 6B show an image of the variations of the elasticity modulus obtained by the Newton-Raphson method regularized according to the Tikhonov method in the case of signal-to-noise ratios equal to 50 and 20, respectively, and in conformity with FIG. 4, for the purpose of comparison with the FIGS. 5A, 5B.
Figure 6B:
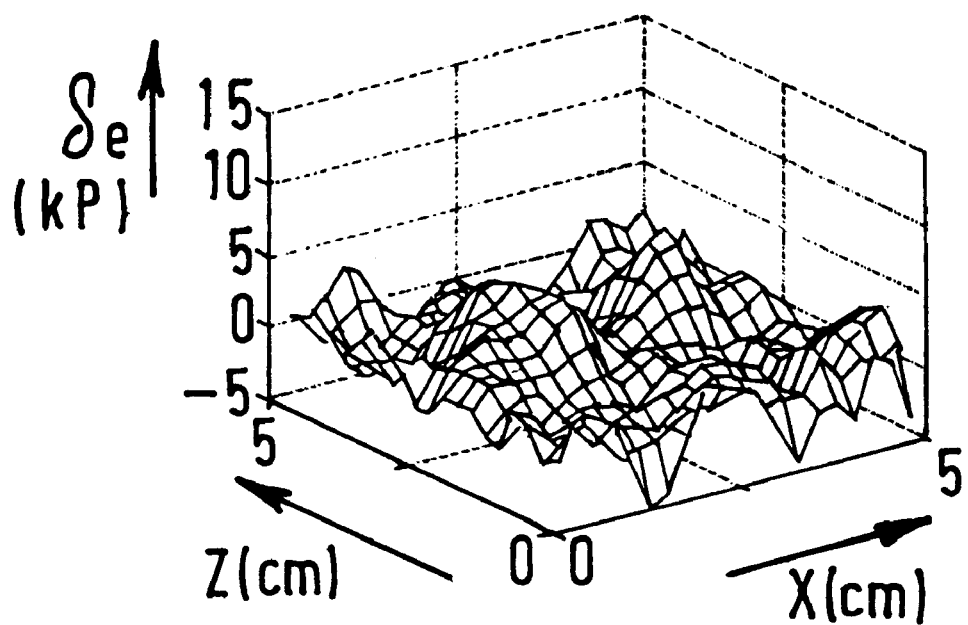

The FIGS. 6A and 6B are reconstructions with the Tikhonov regularization term, realized in otherwise the same conditions as the FIGS. 5A and 5B.

Comparison of the homogeneous tissue zones between the inhomogeneities in the FIGS. 5A and 6A (signal-to-noise ratio equal to 50), reveals that the method according to the invention enables complete noise suppression in these zones, whereas these zones are very noisy when the Tikhonov regularization method is used.

As a result, the images reconstructed according to the invention have a better contrast and the elasticity variations due to inclusions or inhomogeneities of the tissue are better localized and more easily detected.

Moreover, comparison of the homogeneous tissue zones between the inhomogeneities in the FIGS. 5B and 6B (signal-to-noise ratio equal to 20) reveals that the method according to the invention still offers excellent contrast between the various zones, whereas the Tikhonov regularization method offers little contrast; this is a drawback in the applications aimed at the detection of tumors.

An echography apparatus provided with means for carrying out the method illustrated in the FIGS. 1 and 2 thus constitutes an excellent non-invasive means for the detection of tumors, notably for the detection of breast tumors.

What is claimed is:

1. A method of detecting elasticity variations in a soft tissue which is subjected to an external compression in a predetermined axial direction comprising:

estimating a field of axial displacements in the tissue, determining an elasticity modulus estimator, including an operation for minimizing a distance between an image of a distribution of elementary elasticity moduli, by a Finite Element Model, and the field of axial displacements, and regularizating the solution of the estimator by means of a diagonal matrix (R) whose coefficients $[\alpha_{ii}](\alpha_{ii})$ are functions of the axial displacements ($d_i$) which are applied to the respective values of the elementary elasticity moduli ($e_i$) in order to ensure that these elementary elasticity modulus values remain within a uniform interval which is centered around a mean value which is specific to each elementary elasticity modulus.

2. A method as claimed in claim 1, wherein the elasticity modulus estimator is determined by forming a matrix (M) formulated as:

$$M = [S^T S + R]^{-1} S^T,$$

where R is the diagonal regularization matrix and where S is a sensitivity matrix which is a function of the axial displacements, and by performing the matrix multiplication of said matrix (M) by the displacement field vector ($\underline{d}$).

3. A method as claimed in claim 2, further comprising:

coupling an ultrasonic probe associated with an echography apparatus to the soft tissue, said probe emitting the receiving echographic signals parallel to the axial compression direction of the tissue, and estimating the axial displacement field vector in the tissue by utilizing a 1-bit temporal correlation technique for the echographic signals.

4. An echography apparatus for detecting elasticity variations in a soft tissue comprising:

an ultrasonic probe, means for focusing and scanning the probe which is coupled to a reference surface of the tissue and emits and receives echographic signals parallel to an axial direction of the tissue, means for 1-bit correlation of the echographic signals, means for estimating a field of axial displacements in the tissue, a system for estimating the elasticity modulus in order to perform an operation for minimizing a distance between an image of the distribution of elementary elasticity moduli, by a Finite Element Model, and the axial displacement field, and a system for regularizing the solution of the estimator by means of a diagonal matrix (R) whose coefficients ($\alpha_{ii}$) are functions of the axial displacements ($d_i$) and are applied to respective elementary elasticity moduli ($e_i$).

5. An apparatus as claimed in claim 4 further comprising an electronic system for calculating the elasticity modulus estimator by utilizing a matrix (M) formulated as:

$$M = [S^T S + R]^{-1} S^T,$$

where R is the diagonal regularization matrix and where S is a sensitivity matrix which is a function of the axial displacements, and for performing a matrix multiplication of said matrix (M) by the displacement field vector ($\underline{d}$).

6. An apparatus as claimed in claim 5, further comprising an electronic system for the processing of the echographic signals emitted and received by the probe in order to perform a 1-bit temporal correlation of these signals and to produce a field of axial displacements in the soft tissue subjected to the axial external compression.

7. An apparatus as claimed in claim 6 wherein the probe is an array of linear detectors emitting recurrent excitation signals.

8. An apparatus as claimed in claim 4 further comprising:

a system for the formation of echographic images in order to compose medical images on the basis of echographic signals, and an image display system for displaying medical images of the tissue, and for displaying images of the measurements of variations of displacements of the tissue subjected to the continuously variable compression, and for reconstructing images of the distribution of the elasticity modulus in the tissue in order to visualize the elasticity variations in the tissue.

9. An apparatus as claimed in claim 8 wherein the soft tissue comprises tumors, the tumors being associated with the zones of the reconstruction images of the elasticity modulus presenting a contrast of the elasticity variations.

10. An apparatus as claimed in claim 9, wherein the tumors comprise breast cancer, wherein the compressor is provided with means for compressing the breast while applying a radial pressure to a surface of the tissue while, another, parallel surface of the tissue serves as a reference for the radial displacements.

11. An apparatus as claimed in claim 5 further comprising:

a system for the formation of echographic images in order to compose medical images on the basis of echographic signals, and an image display system for displaying medical images of the tissue, and for displaying images of the measurements of variations of displacements of the tissue subjected to the continuously variable compression, and for reconstructing images of the distribution of the elasticity modulus in the tissue in order to visualize the elasticity variations in the tissue.

12. An apparatus as claimed in claim 6 further comprising:

a system for the formation of echographic images in order to compose medical images on the basis of echographic signals, and an image display system for displaying medical images of the tissue, and for displaying images of the measurements of variations of displacements of the tissue subjected to the continuously variable compression, and for reconstructing images of the distribution of the elasticity modulus in the tissue in order to visualize the elasticity variations in the tissue.

* * * * *